United States Patent
Alam et al.

(10) Patent No.: US 10,302,399 B2
(45) Date of Patent: May 28, 2019

(54) BALLISTIC BODY ARMOR DAMAGE SENSING SYSTEM AND RELATED METHODS

(71) Applicant: Ohio University, Athens, OH (US)

(72) Inventors: Khairul Alam, Athens, OH (US); Muhammad Ali, Pickerington, OH (US)

(73) Assignee: Ohio University, Athens, OH (US)

( * ) Notice: Subject to any disclaimer, the term of this patent is extended or adjusted under 35 U.S.C. 154(b) by 0 days.

(21) Appl. No.: 15/406,821

(22) Filed: Jan. 16, 2017

(65) Prior Publication Data
US 2017/0307336 A1    Oct. 26, 2017

Related U.S. Application Data

(60) Provisional application No. 62/365,500, filed on Jul. 22, 2016.

(51) Int. Cl.
| | | |
|---|---|---|
| F41H 1/02 | (2006.01) | |
| A61B 5/00 | (2006.01) | |
| F41J 5/04 | (2006.01) | |

(52) U.S. Cl.
CPC ............ *F41H 1/02* (2013.01); *A61B 5/6805* (2013.01); *A61B 5/7232* (2013.01); *F41J 5/041* (2013.01); *A61B 2503/20* (2013.01)

(58) Field of Classification Search
CPC . F41H 1/02; F41H 1/00; F41H 5/0428; F41H 5/0421; F41H 5/00; A61B 5/7232; A61B 5/6805
See application file for complete search history.

(56) References Cited

U.S. PATENT DOCUMENTS

| | | |
|---|---|---|
| 5,636,378 A | 6/1997 | Griffith |
| 6,349,201 B1 | 2/2002 | Ford |
| 7,609,156 B2 | 10/2009 | Mullen |
| 7,633,052 B2 | 12/2009 | Nakamura et al. |
| 7,660,692 B2 | 2/2010 | Van Albert et al. |
| 7,805,767 B2 | 10/2010 | McElroy et al. |
| 7,954,359 B1 | 6/2011 | Paderewski et al. |
| 8,046,177 B2 | 10/2011 | Liu et al. |

(Continued)

FOREIGN PATENT DOCUMENTS

WO    2015164382 A1    10/2015

OTHER PUBLICATIONS

International Seach Report in International Patent Application No. PCT/US2017/043891, dated Oct. 24, 2017, 4 pgs.

(Continued)

*Primary Examiner* — Toan M Le
(74) *Attorney, Agent, or Firm* — Wood Herron & Evans LLP

(57) ABSTRACT

A ballistic body armor damage sensing system having a body armor ballistic plate including at least one ballistic layer and at least one damage sensing layer coupled to the at least one ballistic layer and including a plurality of electrically conductive members which are positioned throughout said damage sensing layer, wherein when a fired projectile impacts the body armor ballistic plate and damages one or more of the electrically conductive members, the damaged electrically conductive members exhibit a measurable change in electrical resistance.

12 Claims, 11 Drawing Sheets

(56) References Cited

U.S. PATENT DOCUMENTS

| | | | |
|---|---|---|---|
| 8,079,247 B2 | 12/2011 | Russell et al. | |
| 8,265,889 B2 | 9/2012 | Qing et al. | |
| 8,788,218 B2 | 7/2014 | Soles et al. | |
| 8,788,220 B2 | 7/2014 | Soles et al. | |
| 8,886,388 B2 | 11/2014 | Moser et al. | |
| 8,915,118 B2 | 12/2014 | Russell et al. | |
| 8,977,507 B2 | 3/2015 | Soles et al. | |
| 9,081,409 B2 | 7/2015 | Soles et al. | |
| 9,235,378 B2 | 1/2016 | Soles et al. | |
| 9,341,527 B2 | 5/2016 | O'Bier, II et al. | |
| 2007/0260407 A1 | 11/2007 | Van Albert et al. | |
| 2010/0083733 A1* | 4/2010 | Russell | A42B 3/046 |
| | | | 73/12.01 |
| 2011/0089958 A1 | 4/2011 | Malecki et al. | |
| 2012/0188078 A1 | 7/2012 | Soles et al. | |
| 2012/0191376 A1* | 7/2012 | Soles | G08B 13/126 |
| | | | 702/38 |
| 2012/0198593 A1 | 8/2012 | Beck et al. | |
| 2012/0274342 A1 | 11/2012 | Achord | |
| 2016/0005241 A1 | 1/2016 | Soles et al. | |
| 2016/0011064 A1 | 1/2016 | Maybank et al. | |

OTHER PUBLICATIONS

Written Opinion in International Patent Application No. PCT/US2017/043891, dated Oct. 24, 2017, 6 pages.

Acellent's SmartArmor system, Acellent Technologies website—<https://www.acellent.com/industries-2/military>, 2018.

TenCate website—<http://www.tencate.com/amer/advanced-armor/news/TenCate_Smart_Body_Armor.aspx>, 2018.

Smart Body ArmorR, Newport Sensors website—<http://www.newportsensors.com/>, 2015.

* cited by examiner

BALLISTIC BODY ARMOR DAMAGE SENSING SYSTEM AND RELATED METHODS

RELATED APPLICATIONS

The present application claims priority to U.S. Ser. No. 62/368,500 filed Jul. 29, 2016, the disclosure of which is hereby incorporated herein by reference in its entirety.

TECHNICAL FIELD

The present invention relates generally to ballistic body armor, and more particularly, to systems and methods for assessing damage to ballistic body armor caused by fired projectiles.

BACKGROUND

Conventional ballistic body armor implements one or more ballistic plates strategically positioned to overlie a corresponding body region to be protected. For example, a conventional ballistic body armor vest includes a fabric shell that houses at least a ballistic chest plate. The chest plate is supported within the fabric shell such that when a user wears the vest, the chest plate overlies and protects a chest region of the user.

When a fired projectile strikes a body armor ballistic plate, the projectile exerts a force on the ballistic plate. Ideally, the ballistic plate prevents a ballistic penetration and absorbs enough of the ballistic force to prevent serious blunt force trauma to the individual wearing the ballistic plate. However, in various circumstances certain degrees of ballistic force may still be transmitted to the individual and cause bodily injury. The degree of bodily injury suffered is generally directly proportional to the amount of ballistic force exerted on the individual.

In military operations, there is a need to provide efficient medical assistance to soldiers injured in the field. In this regard, it is imperative to quickly assess the extent of bodily injury suffered by a solider impacted by a fired projectile so that appropriate treatment actions may be taken quickly, particularly when there are multiple critically injured soldiers in need of treatment and limited medical resources are available. Accordingly, there is a need for improvements to conventional ballistic body armor to assist in enabling swift assessment of bodily injury experienced by an individual struck by a fired projectile, and thereby enable efficient provision of medical treatment.

BRIEF DESCRIPTION OF THE DRAWINGS

The drawings, which are incorporated in and constitute a part of this specification, illustrate exemplary embodiments of the invention and, together with the detailed description given below, serve to explain the exemplary embodiments. Like reference numerals are used to indicate like features throughout the various figures of the drawings, wherein.

DETAILED DESCRIPTION

Referring to FIGS. 1-4, a ballistic body armor damage sensing system 10 according to exemplary embodiment of the invention is shown. The damage sensing system 10 provides progressive damage assessment of one or more body armor ballistic plates 12, such as a torso plate, worn by an individual, such as a soldier, for protection from ballistic impacts. More specifically, the damage sensing system 10 detects and records ballistic force exerted on the body of the individual by a fired projectile that impacts the ballistic plate 12.

Figure 1:
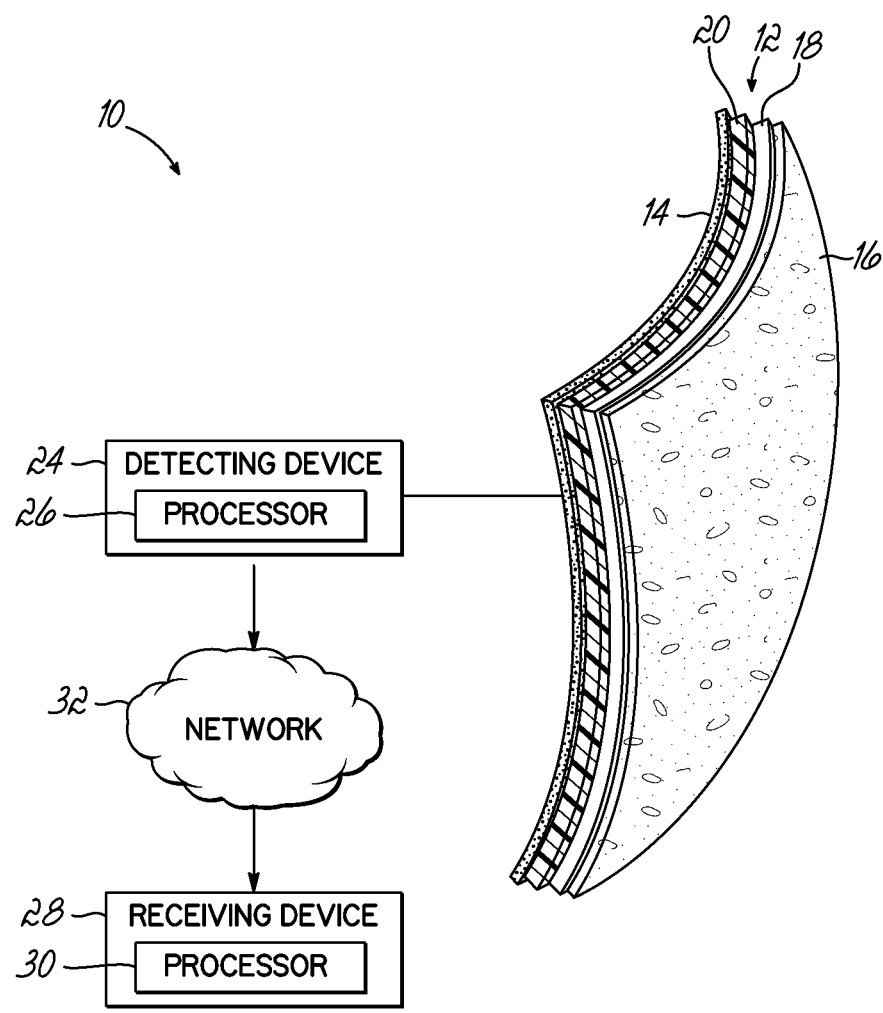
FIG. 1 is a schematic front isometric view of a ballistic body armor damage sensing system according to an exemplary embodiment of the invention.
Figure 2:
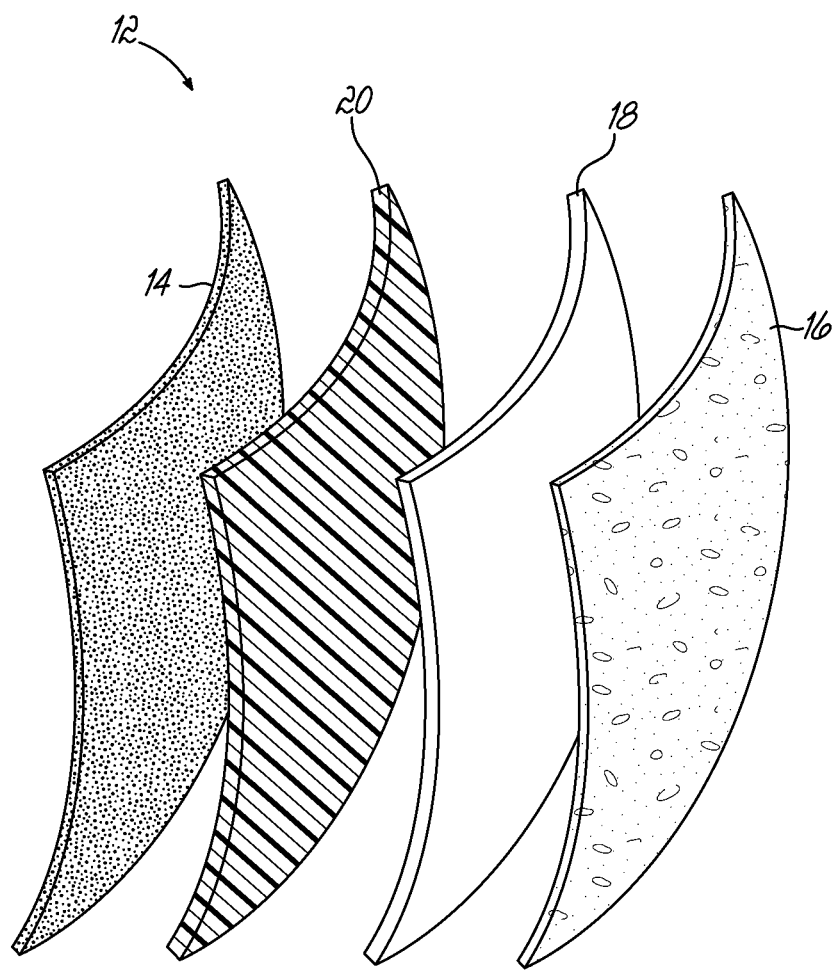
FIG. 2 is an exploded front isometric view of a ballistic plate and damage sensing layer of the ballistic body armor damage sensing system of FIG. 1.
Figure 3:
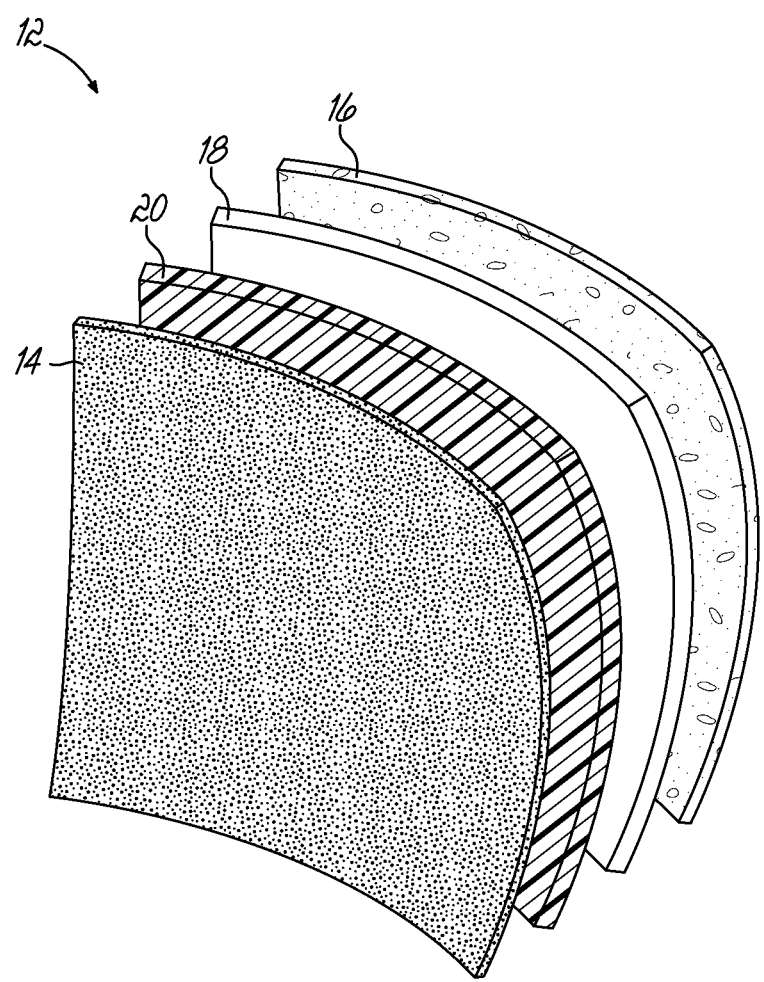
FIG. 3 is an exploded rear isometric view of the ballistic plate and damage sensing layer.
Figure 4:
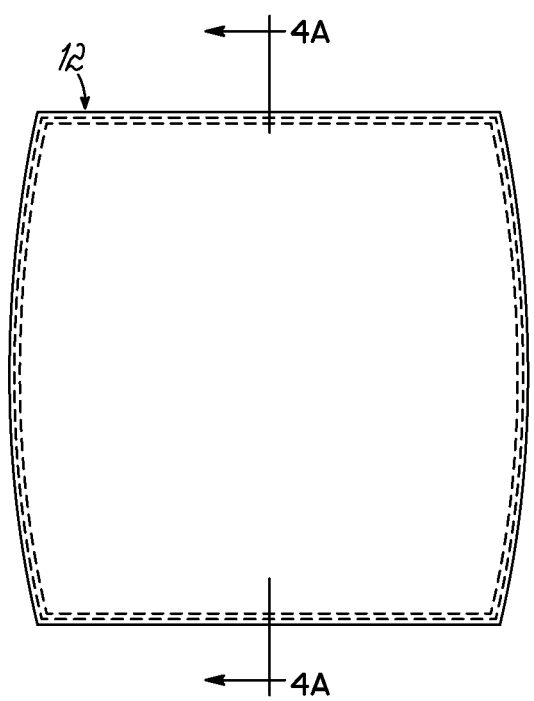
FIG. 4 is a front elevation view and a corresponding side cross-sectional view of the ballistic plate and damage sensing layer.
Figure 4A:
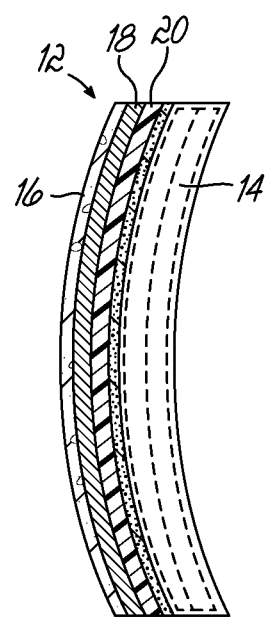
FIG. 4A is a cross-sectional view taken at lines 4a-4a of FIG. 4.

The damage sensing system 10 includes at least one damage sensing layer 14 coupled to an exterior surface of, or integrated within, the ballistic plate 12, and configured to identify a projectile impact of the ballistic plate 12. As shown in FIGS. 1 and 2, the ballistic plate 12 may include a plurality of layers. In an exemplary embodiment, these plate layers may include a strike plate 16 defining a front face of the ballistic plate 12, a ceramic core layer 18 positioned behind the strike plate 16, and a back plate 20 positioned behind the ceramic layer 18 and defining a rear face of the ballistic plate 12. The plate layers 16, 18, 20 may be bonded to one another using any suitable method known in the art. In one embodiment, the damage sensing layer 14 may be coupled to the rear face of the back plate 20 so as to directly confront the body of a user when the ballistic plate 12 is worn.

Figure 6A:
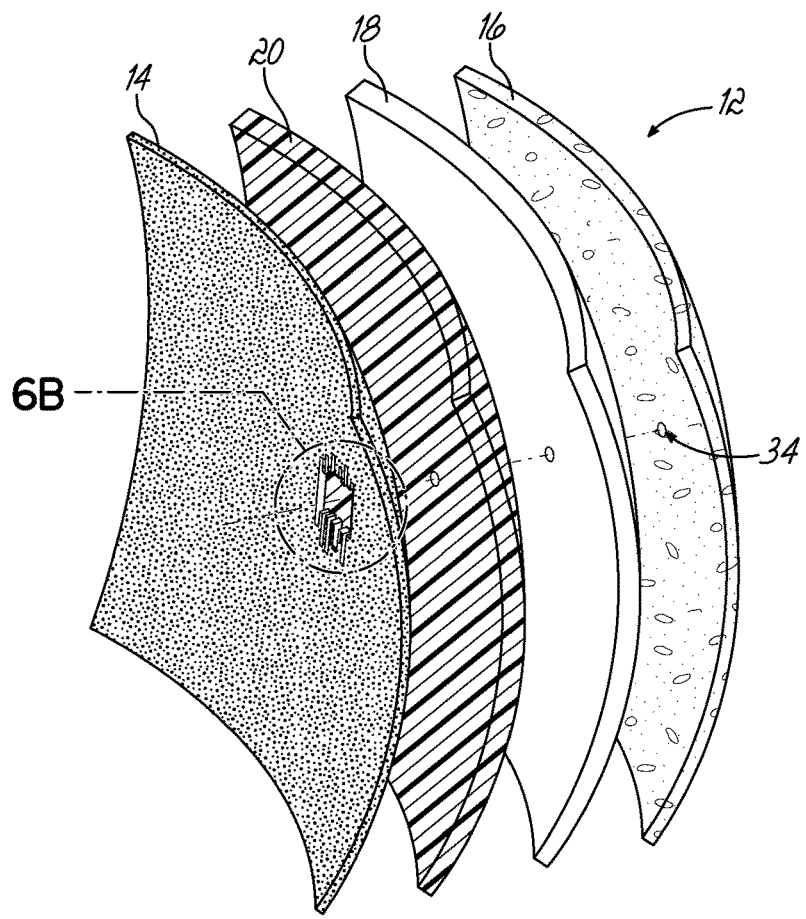
FIG. 6A is an exploded rear isometric view of the pierced ballistic plate and damage sensing layer of FIG. 5.
Figure 6B:
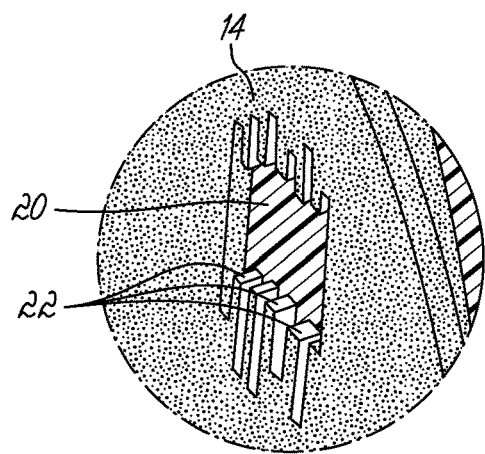
FIG. 6B is an enlarged view of the pierced damage sensing layer of FIG. 6A, showing details of damaged electrically conductive members of the damage sensing layer.

Referring briefly to FIG. 6B, the damage sensing layer 14 includes a plurality of electrically conductive members having a known electrical resistance. In the exemplary embodiments illustrated in the Figures, the electrically conductive members are shown in the form of elongate fibers 22. However, it will be appreciated that in alternative embodiments the electrically conductive members may be non-fiber members, such as metal wires or polymeric elements, for example.

In exemplary embodiments, the electrically conductive fibers 22 may be carbon fibers arranged unidirectionally within the damage sensing layer 14. Advantageously, carbon has a natural electrical resistance that is easily measured with standard electrical measuring equipment. Additionally, carbon provides a particularly strong and rigid yet lightweight construction. In alternative embodiments, the electrically conductive fibers 22 may be formed from other electrically conductive materials, such as a material that has been modified to have an electrical resistance similar to that of carbon.

Referring back to FIG. 1, the damage sensing system 10 may further include a detecting device 24 having a processor 26, a receiving device 28 having a processor 30, and a network 32 over which the detecting and receiving devices 28 communicate. In exemplary embodiments, the detecting device 24 and/or the receiving device 28 may include software, firmware, hardware, or any combination thereof. The detecting device 24 is electrically coupled to the damage sensing layer 14, for example at one or more electrodes (not shown), and measures an electrical resistance of the damage sensing layer 14. Specifically, the detecting device 24 may detect and measure an electrical current flowing through the damage sensing layer 14.

Figure 5:
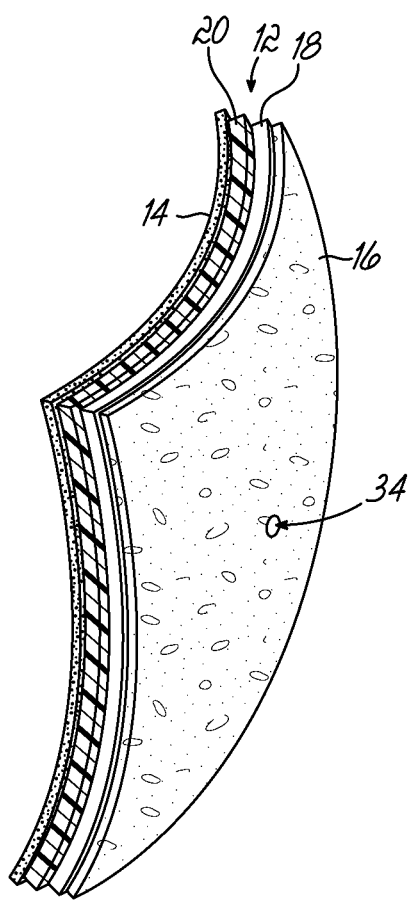
FIG. 5 is a front isometric view of a ballistic plate and damage sensing layer after having been pierced by a fired projectile.

As shown in FIGS. 5-6B, a projectile fired at the ballistic plate 12 may pierce the layers 16, 18, 20 of the plate 12, creating an impact bore 34 therethrough, so as to impact and damage one or more of the electrically conductive fibers 22 of the damage sensing layer 14, as shown best in FIG. 6B. As a result of the one or more conductive fibers 22 being damaged, the damage sensing layer 14 undergoes a measurable change (e.g., increase) in electrical resistance, and thus exhibits a new electrical resistance post-impact. This change in electrical resistance is detected by the detecting device 24, which then generates a signal corresponding to the change in electrical resistance, and transmits the signal to the receiving device 28 over the network 32. For example, the detecting device 24 may detect the change in electrical resistance, measure the new electrical resistance, and generate a signal indicating the new electrical resistance. Generation and transmission of the signal by the detecting device 24 may be performed immediately upon an impact of the damage sensing layer 14 by a fired projectile.

In an exemplary embodiment, the receiving device 28 may be in the form of a monitoring station located remotely from the ballistic plate 12, such as at a military base site. The receiving device 28 may include a user interface (not shown), which may include any suitable type of display device including, but not limited to, a touch screen display, a cathode ray tube (CRT) monitor, or a liquid crystal display (LCD) screen, for example. Transmission of the signal from the detecting device 24 to the receiving device 28 is performed over the network 32, which may be a wide area network (WAN) or a local area network (LAN), for example. In one embodiment, the network 32 may be a wireless network, such as a wireless LAN (WLAN, or "Wi-Fi") for example, over which transmission of the signal is performed wirelessly. It will be appreciated that a plurality of detecting devices 24 assigned to a corresponding plurality of body armor ballistic plates 12 may communicate with a single receiving device 28 over the network 32.

Upon receiving the signal generated by the detecting device 24, the receiving device 28 may compare electrical data indicated by the signal to known electrical values stored within a database accessible to the receiving device 28. The database may include: (i) a plurality of measured ballistic forces of various quantities exerted by fired projectiles impacting a damage sensing layer 14 of the type incorporated in the damage sensing system 10 and causing a corresponding degree of damage to the electrically conductive fibers 22 of the damage sensing layer 14; and (ii) a corresponding plurality of electrical resistances exhibited by the damage sensing layer 14 experiencing that degree of damage to the electrically conductive fibers 22.

In an exemplary embodiment, the receiving device 28 may identify an electrical resistance value within the referenced database that is closest in magnitude to the electrical resistance detected by the detecting device 24, and identify the corresponding ballistic force stored in the database. If the detected electrical resistance value lies between two electrical resistance values stored in the database, the receiving device may extrapolate the database values using known methods to determine a ballistic force value that corresponds to the detected electrical force value. The receiving device 28 may then display the determined ballistic force value to a user, or it may compare the determined ballistic force value to one or more predetermined ballistic force values to determine an anticipated degree of bodily injury suffered by the individual wearing the ballistic plate 12.

Advantageously, the signal transmission and data evaluation process described above provides the user of the receiving device 28, such as a medical professional, immediate information for gauging the severity of bodily injury incurred by an individual wearing the ballistic plate 12, so that appropriate medical response actions may be taken quickly thereafter. For example, in an exemplary application in which a plurality of soldiers each wearing body armor including a ballistic plate 12 having a damage sensing layer 14 are struck through the ballistic plates 12 by fired projectiles, a medical professional monitoring the receiving device 28 may quickly and remotely determine which of the soldiers are likely to have incurred the most severe bodily injury, and thus plan an appropriate medical response.

Figure 7A:
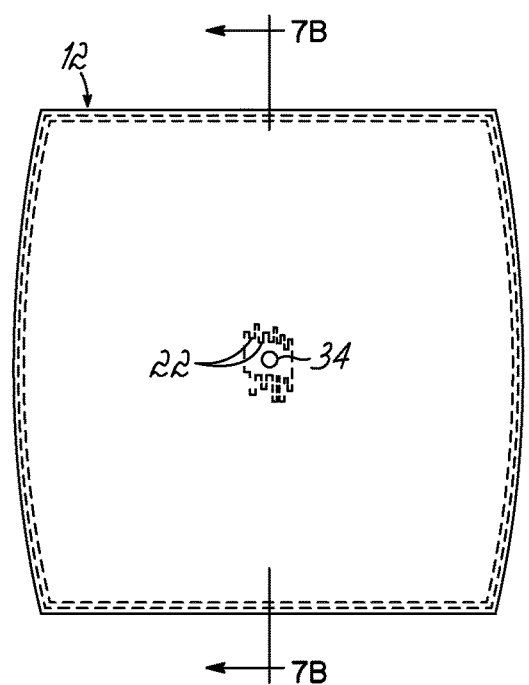
FIG. 7A is a rear elevation view of the pierced ballistic plate and damage sensing layer of FIG. 5.
Figure 7B:
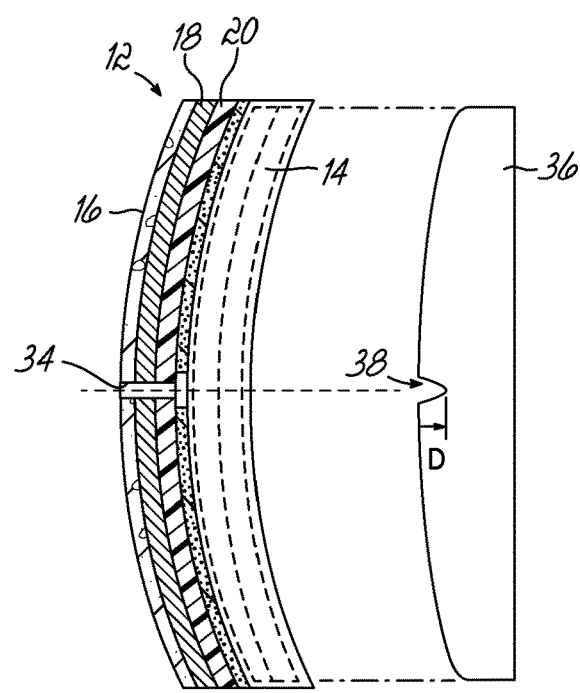
FIG. 7B is a side cross-sectional view of the pierced ballistic plate and damage sensing layer shown in combination with a layer of ballistic clay applied to the damage sensing layer for acquisition of baseline data.

The measured ballistic forces and corresponding electrical resistances stored in the database referenced by the receiving device 28 may be obtained through testing procedures using ballistic clay, such as Roma Plastilina No. 1 clay, for example. In an exemplary embodiment, as shown in FIG. 7B, a layer 36 of ballistic clay may be applied to the rear face of the damage sensing layer 14 that would be positioned to confront the body of an individual wearing the ballistic plate 12. A projectile, such as a bullet, may then be fired directly at the ballistic plate 12 to pierce the forward layers 16, 18, 20 of the ballistic plate 12 and impact the damage sensing layer 14 so as to create a depression 38 of depth D in the clay layer 36. Consulting a known relationship between ballistic force and depth D of the depression 38, a corresponding ballistic force that caused the depression 38 can be determined. Additionally, using the detecting device 24 or other device suitable for measuring electrical resistance, an electrical resistance of the impacted damage sensing layer 14 may be measured and logged in connection with the determined ballistic force. This process may be repeated as many times as desired under varying conditions to generate a database of electrical resistances and corresponding ballistic forces, which may be referenced by the receiving device 28 in the field during operation.

Information transmitted by the detecting device 24 to the receiving device 28 may also be implemented to inform of the current structural integrity of the ballistic plate 12. In that regard, one or more damage sensing layers 14 may be coupled to or integrated within the ballistic plate 12 at various locations as desired. For example, a damage sensing layer 14 may be provided at the front face of the strike plate 16. Structural integrity of the strike plate 16, and thus of the ballistic plate 12 as a whole, may be evaluated based on the change (e.g., increase) in electrical resistance exhibited by the damage sensing layer 14 as the ballistic plate 12 is struck by one or more fired projectiles. Degree of damage caused to the electrically conductive fibers 22 of the damage sensing layer 14, and the resulting change in electrical resistance, may also inform of a velocity of the fired projectile.

Figure 8:
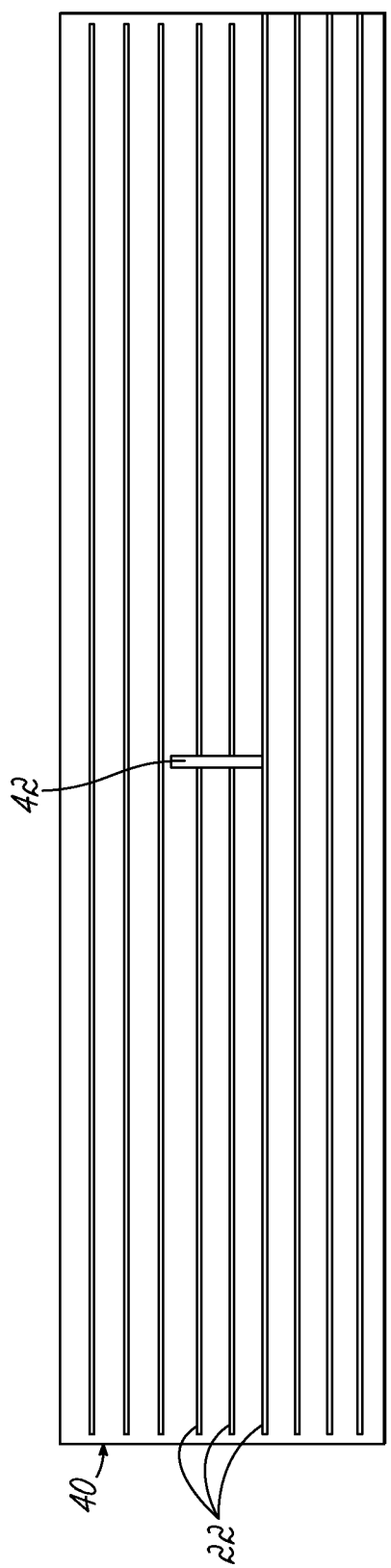
FIG. 8 is a top elevation view of a damage sensing layer having electrically conductive members that were cut during testing to simulate damage by a projectile.
Figure 9:
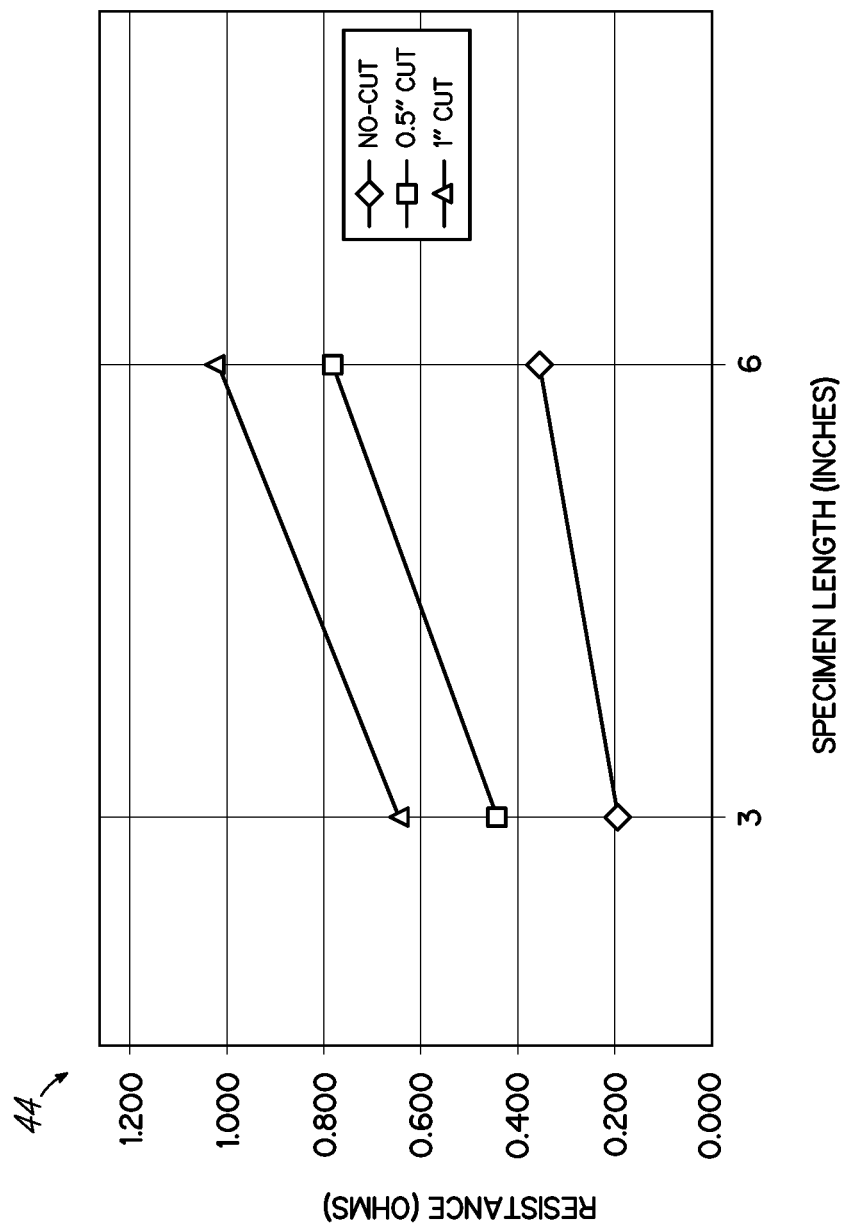
FIG. 9 is a line graph showing an exemplary relationship between length of a damage sensing layer having cuts of various length and corresponding electrical resistance of the cut damage sensing layer.

Referring to FIG. 8, an experimental damage sensing layer 40 formed from carbon fibers 22 arranged unidirectionally is shown. Cuts 42 having lengths of approximately 0.5 inches and 1.0 inches were manually formed in a central region of the damage sensing layer 14, and the electrical resistance of the damage sensing layer 14 was measure before and after the cuts 42 were made. The observed relationship between length of the damage sensing layer 40, length of the cut 42 formed in the layer 40, and resulting electrical resistance of the damage sensing layer 40 is represented in the line graph 44 shown in FIG. 9. As shown in the line graph 44, electrical resistance of the damage sensing layer 14 increases proportionally with damage incurred by the damage sensing layer 40.

Figure 10A:
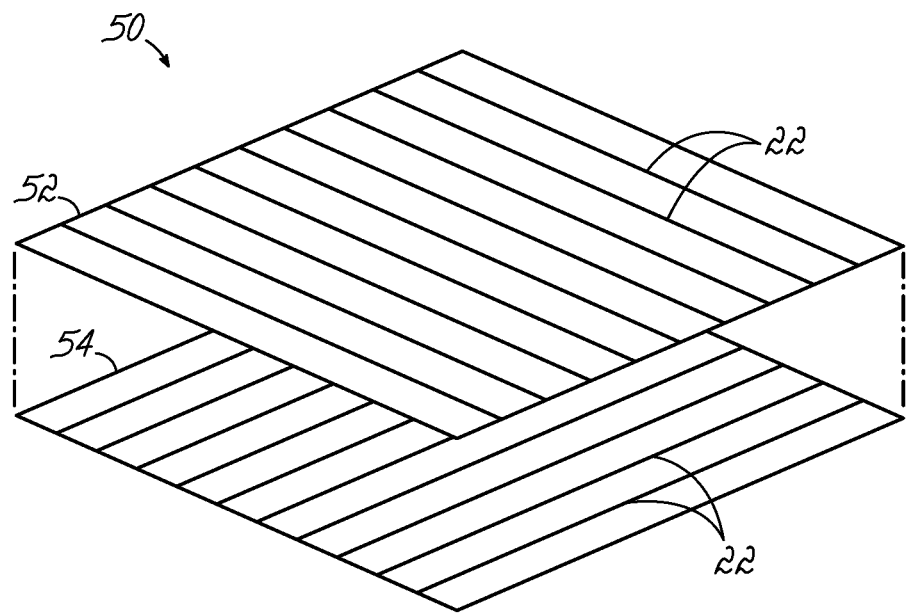
FIG. 10A is a schematic isometric view of first and second damage sensing layers having electrically conductive members extending in respective first and second directions.
Figure 10B:
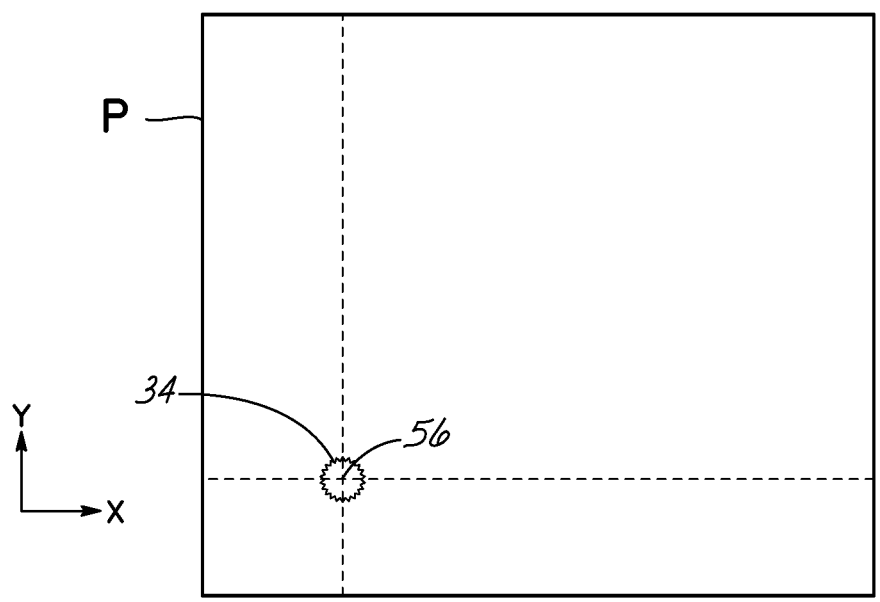
FIG. 10B is a top elevation view of the first and second damage sending layers of FIG. 10A, with a schematic representation of a projectile impact location in a plane.

Referring to FIGS. 10A and 10B, a plurality of damage sensing layers may be provided and arranged to enable location of a projectile impact site created by a fired projectile in a plane defined by the damage sensing layers. As shown in FIG. 10A, an exemplary arrangement 50 includes a first and second damage sensing layers 52, 54, each of which may be similar in construction to damage sensing layer 14. The first damage sensing layer 52 has a first plurality of electrically conductive fibers 22 arranged unidirectionally in a first fiber direction, and a second damage sensing layer 54 has a second plurality of electrically conductive fibers 22 arranged unidirectionally in a second fiber direction. The first and second fiber directions may be generally perpendicular to one another so as to define first and second axes (e.g., X and Y) of a plane P defined by the first and second layers 52, 54. The first and second layers 52, 54 may be bonded to an outer surface of a ballistic plate 12 or integrated within the ballistic plate 12 and arranged between the plate layers 16, 18, 20. Additionally, the first and second layers 52, 54 may be positioned adjacent to one another or spaced apart. For example, the first and second layers 52, 54 may be separated by one or more of the plate layers 16, 18, 20.

In response to a fired projectile piercing the ballistic plate 12 and damaging electrically conductive fibers 22 of the first and second damage sensing layers 52, 54, the detecting device 24 may determine a location in the plane P of an impact site 56 of the fired projectile. In particular, the detecting device 24 may first determine a location of damaged electrically conductive fibers 22 of the first damage sensing layer along a direction perpendicular to the first fiber direction. This step provides a first Cartesian coordinate, such as an "X" coordinate, of the impact site 56 in the plane P. The detecting device may then determine a location of damaged electrically conductive fibers 22 of the second damage sensing layer 14 along a direction perpendicular to the second fiber direction. This step provides a second Cartesian coordinate, such as a "Y" coordinate, of the impact site 56 in the plane P.

The detecting device 24 may then transmit the first and second coordinates, informing of the impact site location in the plane P, to the receiving device 28. In turn, the receiving device 28 may display or otherwise communicate this location to a user monitoring the receiving device 28. In this manner, the user may be informed of a general location of potential injury on the body of an individual wearing the ballistic plate 12, and quickly response with appropriate medical treatment action.

In alternative embodiments, any desired quantity of damage sensing layers similar to layers 52, 54 may be provided. Additionally, while damage sensing layers 52, 54 are oriented so as to yield first and second fiber directions that perpendicular to one another, and thereby define first and second axes of a Cartesian coordinate system, various alternative configurations may be provided that are suitable to enable location of an impact site using any desired coordinate system type. In that regard, any desired quantity of damage sensing layers may be provided, which may be arranged to yield any desired fiber directions.

Figure 11:
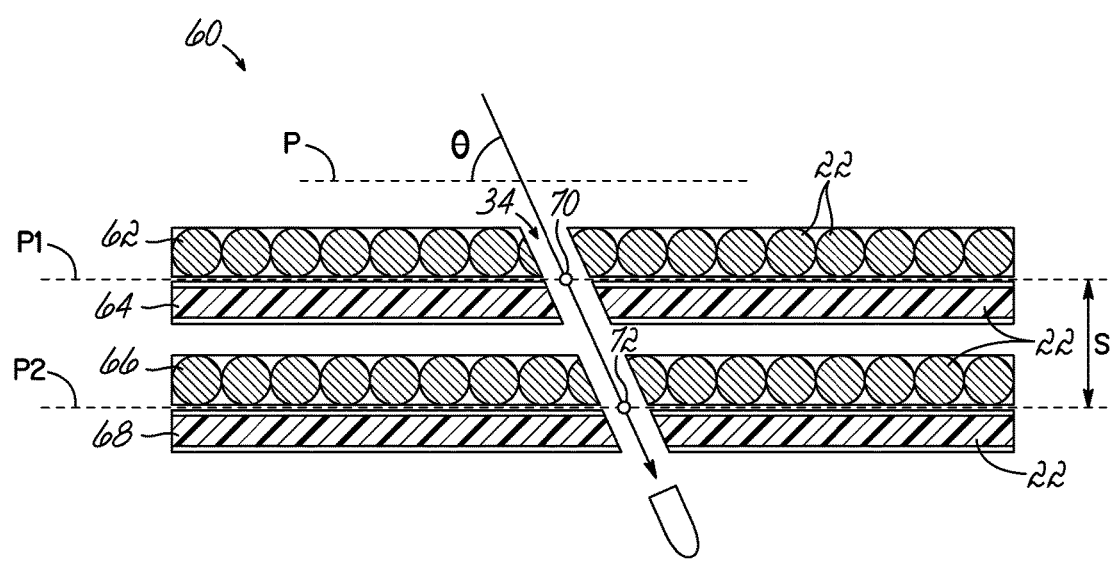
FIG. 11 is a schematic side cross-sectional view of an arrangement of a damage sensing layers according to an exemplary embodiment of the invention that enables determination of a trajectory angle of a fired projectile.

Referring to FIG. 11, a plurality of damage sensing layers may be provided and arranged to enable determination of a trajectory angle θ relative to a reference plane P of a fired projectile that pierced the ballistic plate 12. FIG. 11 shows an exemplary arrangement 60 including first, second, third, and fourth damage sensing layers 62, 64, 66, 68, each of which may be similar in construction to damage sensing layer 14. In exemplary embodiments, the damage sensing layers 62, 64, 66, 68 may be integrated within the ballistic plate 12 and interspaced among the plate layers 16, 18, 20. For example, as shown, the first and second damage sensing layers 62, 64 may be positioned immediately adjacent to one another and spaced apart from the third and fourth damage sensing layers 66, 68, which may be positioned immediately adjacent to one another.

The damage sensing layers 62, 64, 66, 68 may be oriented such that the fiber direction defined by each damage sensing layer 14 is perpendicular to the fiber direction defined by each adjacent damage sensing layer 14. For example, as shown in FIG. 11, the first and third damage sensing layers 62, 66 may be oriented similarly to one another such that their electrically conductive fibers 22 extend in a first fiber direction, while the second and fourth damage sensing layers 64, 66 may be oriented similarly to one another such that their electrically conductive fibers 22 extend in a second fiber direction.

Using the method described above in connection with FIGS. 10A and 10B, the detecting device 24 may determine a location of a first impact site 70 in a first impact plane P1 defined by the adjacent first and second damage sensing layers 62, 64, and a location of a second impact site 72 in a second impact plane P2 defined by the adjacent third and fourth damage sensing layers 66, 68. The trajectory angle θ of the fired projectile relative to a reference plane P may then be calculated using the locations of these first and second impact sites 70, 72 and a known spacing S between the first and second impact planes P1, P2. This determination may be performed by the detecting device 24 or by the receiving device 28, and then communicated by the receiving device 28 to a user monitoring the receiving device 28. In exemplary applications, the projectile trajectory angle θ may inform of the general location of an enemy shooter who fired the projectile, and/or which internal organs of the individual wearing the ballistic plate 12 may have been injured by the fired projectile.

In an exemplary embodiment, the third and fourth damage sensing layers 66, 68, or alternatively an additional set of damage sending layers, may be coupled to the rear face of the back plate 20 of the ballistic plate 12, so that the location of the second impact site 72 may inform of the approximate location of bodily injury on the individual wearing the ballistic plate 12.

In an arrangement (not shown) according to another exemplary embodiment of the invention, a plurality of damage sensing layers 14 may be arranged, for example immediately adjacent to one another, such that each layer 14 corresponds to a respective, distinct region of the ballistic plate 12. Accordingly, the location of a projectile impact site on the ballistic plate 12 may be determined by identifying, with the detecting device 24, which of the damage sensing layers 14 has undergone a change in electrical resistance so as to indicate that it has been impacted and damaged by the fired projectile. In scenarios in which a fired projectile impacts and damages the boundary at which two or more adjacent damage sensing layers 14 meet, each of those damage sensing layers 14 will be identified by the detecting device 24 as having been impacted. This identification allows for a determination, for example by the receiving device 28 or by an individual monitoring the receiving device 28, that the projectile impact site is located along the boundary between the multiple damage sensing layers 14.

It has been observed that a projectile impact to an edge portion of a ballistic plate 12 may yield a different type and/or degree of damage to the plate 12, potentially resulting in a different type and/or degree of bodily injury to the individual wearing the ballistic plate 12, than a similar projectile impact to a central portion of the ballistic plate 12. Further, in embodiments in which multiple ballistic plates 12 are arranged adjacent to one another, a projectile impact causing damage to an edge portion of a first ballistic plate 12 may simultaneously cause damage to an adjacent edge portion of a second ballistic plate 12 arranged adjacent to the first ballistic plate 12.

Multiple sensing layers 14, such as those shown in FIG. 1, can be arranged adjacent each other. Electrically conductive fibers 22 of one or more damage sensing layers 14 of a ballistic plate 12 may be suitably arranged, for example coupled together, so as to enable the detecting device 24 to identify and distinguish a plate edge portion impact from a plate central portion impact. As an example, several unidirectional carbon fiber layers may be joined electrically at the each ends of the ballistic plate, thus forming a rectangular measurement section, and the resistance values between different pairs of corner points of this rectangle can be used to detect impact damage at edges of the plate. The detecting device 24 may also identify and log a plate edge portion impact of a first ballistic plate 12 in connection with a plate edge portion impact of one or more adjacent ballistic plates 12 impacted by the same fired projectile. In the signal generated by the detecting device 24 for communication to the receiving device 28, as described above, the detecting device 24 may include information corresponding to the plate edge portion impacts.

Operationally, data captured by the ballistic body armor damage sensing system 10 disclosed herein may be used for Battlefield Damage and Assessment Reporting. For example, evaluation of ballistic forces exerted and projectile fragments embedded in a damaged ballistic plate 12 can be used to determine an enemy threat, and engagement ranges can be extrapolated through ballistic curves to better understand when, how, and from what range a ballistic incident occurred. Additionally, the system 10 can be used to understand ballistic force as it propagates through the plate layers 16, 18, 20 of the ballistic plate 12.

As described above, an objective of the ballistic body armor damage sensing system 10 is to utilize a correlation of damage to conductive fibers 22 on a body-side of the ballistic plate 12 to ballistic force exerted, using a known relationship between ballistic force and deformation of ballistic clay. The damage to conductive fibers 22 may be measured via a change in resistance or current due to broken fibers 22 on the body side of the ballistic plate 12. Once a suitable baseline has been established, trauma due to a ballistic impact in the field can be compared to this data.

It has been established in many ballistic testing protocols that a 44 mm depression due to a ballistic impact is the limit that is survivable by a human being. Using the ballistic body armor damage sensing system 10, when an individual experiences a ballistic impact on the ballistic plate 12, a measurement is taken assessing the amount of trauma that has been transferred to the individual compared to data that has been gathered using the ballistic clay. A user may identify whether the impact has caused a degree to bodily trauma equal to or greater than the amount of trauma that yields a 44 mm deep impact into the ballistic clay. This process may inform if urgent medical assistance for the individual is necessary, or if the impact trauma was minimal and serious injury is unlikely. Secondary functions of the system 10 may be to communicate to others that a fellow user has been injured.

As described above, another objective of the ballistic body armor damage sensing system 10 is to identify a location of the projectile impact site. In exemplary applications, the identified impact site location may be applied to a body diagram, such as a two-dimensional 90th percentile silhouette of the individual, to identify projectile impact location and severity with respect to the location of vital bodily organs. In exemplary embodiments, the projectile penetration or intensity of damage may be extracted from a crater formation/shear plugging or bulging observed on the back plate 20 of the ballistic plate 12.

While the present invention has been illustrated by the description of specific embodiments thereof, and while the embodiments have been described in considerable detail, it is not intended to restrict or in any way limit the scope of the appended claims to such detail. The various features discussed herein may be used alone or in any combination. Additional advantages and modifications will readily appear to those skilled in the art. The invention in its broader aspects is therefore not limited to the specific details, representative apparatus and methods and illustrative examples shown and described. Accordingly, departures may be made from such details without departing from the scope of the general inventive concept.

What is claimed is:

1. A ballistic body armor damage sensing system, comprising:
   a body armor ballistic plate including at least one ballistic layer; and
   at least one damage sensing layer coupled to the at least one ballistic layer and including a plurality of electrically conductive members, positioned throughout said damage sensing layer,
   wherein when a fired projectile impacts the body armor ballistic plate and damages one or more of the electrically conductive members, the damaged electrically conductive members exhibit a measurable change in electrical resistance, and wherein the electrically conductive members include carbon fibers.

2. The ballistic body armor damage sensing system of claim 1, further comprising:
a detecting device that detects the change in electrical resistance of the damaged electrically conductive members and generates a signal corresponding to the change in electrical resistance.

3. The ballistic body armor damage sensing system of claim 1, wherein the electrically conductive members are arranged unidirectionally.

4. The ballistic body armor damage sensing system of claim 1, wherein the at least one damage sensing layer includes a first damage sensing layer having a first plurality of electrically conductive members arranged unidirectionally in a first member direction, and a second damage sensing layer having a second plurality of electrically conductive members arranged unidirectionally in a different second member direction, and wherein in response to the fired projectile damaging electrically conductive members in the first and second damage sensing layers, the detecting device identifies a location of damaged electrically conductive members within the first damage sensing layer along a direction perpendicular to the first member direction, and a location of damaged electrically conductive members with the second damage sensing layer along a direction perpendicular to the second member direction.

5. The ballistic body armor damage sensing system of claim 4, wherein in response to identifying the locations of the damaged electrically conductive members within the first and second damage sensing layers, the system determines a location of a projectile impact site in a plane defined by the body armor ballistic plate.

6. The ballistic body armor damage sensing system of claim 4, wherein in response to identifying the locations of the damaged conductive members within the first and second damage sensing layers, the system determines a trajectory angle of the fired projectile.

7. A method of assessing damage caused by a fired projectile striking ballistic body armor including at least one damage sensing layer impacted by the fired projectile, the method comprising:
detecting, with a detecting device, an electrical characteristic of the at least one damage sensing layer having electrically conductive members damaged by the fired projectile, wherein the detected electrical characteristic includes at least one of electrical resistance or electrical current and wherein the electrically conductive members include carbon fibers;
generating, with the detecting device, a signal corresponding to the detected electrical characteristic; and
transmitting, with the detecting device, the signal to a receiving device.

8. The method of claim 7, further comprising in response to receiving the signal, comparing the detected electrical characteristic to a known electrical characteristic value corresponding to a predetermined ballistic force value.

9. The method of claim 7, wherein transmitting the signal to the receiving device includes wirelessly transmitting the signal.

10. The method of claim 7, further comprising identifying an edge portion of a ballistic plate, to which the damage sensing layer is coupled, damaged by the fired projectile.

11. The method claimed in claim 7 wherein said body armor includes a second sensing layer and said method comprises detecting an electrical characteristic of said second sensing layer having electrically conductive members damaged by the fired projectile and comparing information from said first and second sensing layer to determine the location where said projectile struck said body armor.

12. The method claimed in claim 7 wherein a plurality of soldiers are wearing said armor and a plurality of signals are received by said receiving device to allow damage to multiple body armors to be compared to determine soldiers in need of immediate attention.

* * * * *

UNITED STATES PATENT AND TRADEMARK OFFICE
CERTIFICATE OF CORRECTION

| | |
|---|---|
| PATENT NO. | : 10,302,399 B2 |
| APPLICATION NO. | : 15/406821 |
| DATED | : May 28, 2019 |
| INVENTOR(S) | : Khairul Alam et al. |

It is certified that error appears in the above-identified patent and that said Letters Patent is hereby corrected as shown below:

In the Specification

| | | |
|---|---|---|
| Column 1, Lines 15-16, "body armor, and more particularly, to" | should read | --body armor and, more particularly, to-- |
| Column 2, Line 4, "view taken along lines 4a-4a" | should read | --view taken along line 4a-4a-- |
| Column 2, Line 34, "damage sending layers" | should read | --damage sensing layers-- |
| Column 2, Line 36, "arrangement of a damage sensing" | should read | --arrangement of damage sensing-- |
| Column 6, Line 13, "quickly response with" | should read | --quickly respond with-- |
| Column 6, Line 19, "directions that perpendicular to" | should read | --directions perpendicular to-- |
| Column 7, Line 50, "at the each ends of the ballistic" | should read | --at each end of the ballistic-- |
| Column 8, Lines 24-25, "caused a degree to bodily trauma" | should read | --caused a degree of bodily trauma-- |

In the Claims

| | | |
|---|---|---|
| Claim 11, Column 10, Lines 31-32, "second sensing layer to determine" | should read | --second sensing layers to determine-- |

Signed and Sealed this
Third Day of September, 2019

Andrei Iancu
*Director of the United States Patent and Trademark Office*